(12) United States Patent
Bird

(10) Patent No.: US 6,306,112 B2
(45) Date of Patent: Oct. 23, 2001

(54) BLADDER FOR ORTHOPEDIC SUPPORTS

(75) Inventor: John R. Bird, St. Paul, MN (US)

(73) Assignee: Bird & Cronin, Inc., Eagan, MN (US)

( * ) Notice: Subject to any disclaimer, the term of this patent is extended or adjusted under 35 U.S.C. 154(b) by 0 days.

(21) Appl. No.: 09/243,070

(22) Filed: Feb. 2, 1999

(51) Int. Cl.[7] .................................................. A61F 5/00
(52) U.S. Cl. .................................. 602/27; 602/6; 602/7; 602/8; 602/12
(58) Field of Search ............................... 602/5–7, 13, 23, 602/27, 12, 78

(56) References Cited

U.S. PATENT DOCUMENTS

| Re. 34,661 | * | 7/1994 | Grim . |
| 4,964,402 | * | 10/1990 | Grim et al. . |
| 5,014,691 | * | 5/1991 | Cueman et al. . |
| 5,695,452 | * | 12/1997 | Grim et al. . |

* cited by examiner

Primary Examiner—Michael A. Brown
Assistant Examiner—Lalita M Hamilton
(74) Attorney, Agent, or Firm—Merchant & Gould, P.C.

(57) ABSTRACT

A therapeutic ankle support brace bladder pad member having a pair opposed surfaces defining an inflated air support pocket and a second support pocket containing gel material and filler apparatus materials, is disclosed. An overlay fabric material is integrally attached to the bladder, provides additional support and enables removable attachment of the bladder to side support members of a therapeutic brace.

17 Claims, 3 Drawing Sheets

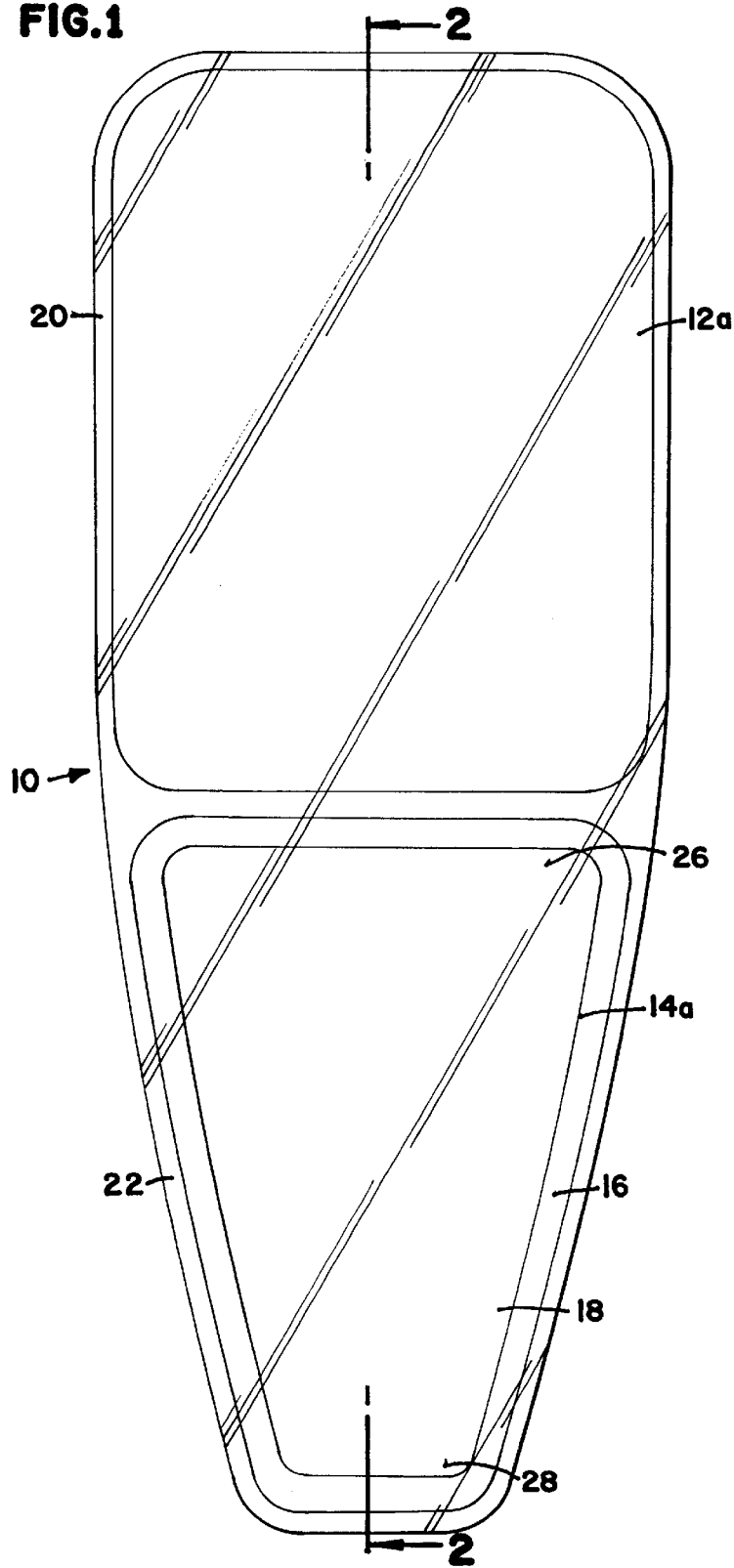
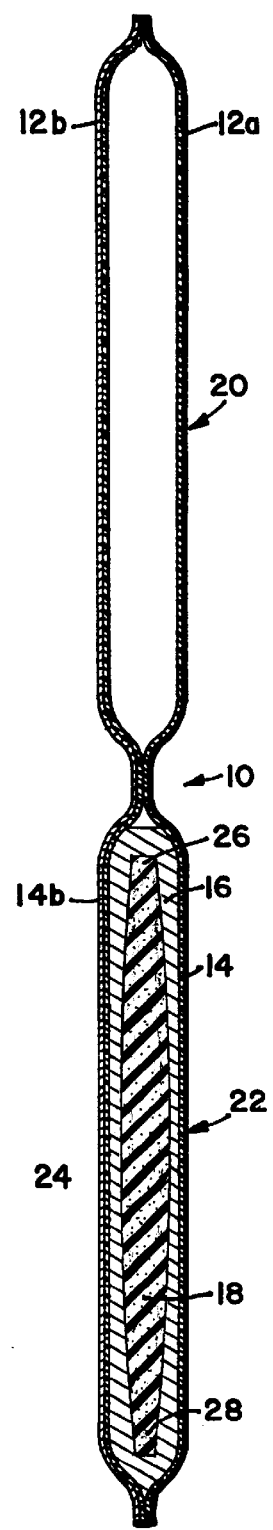

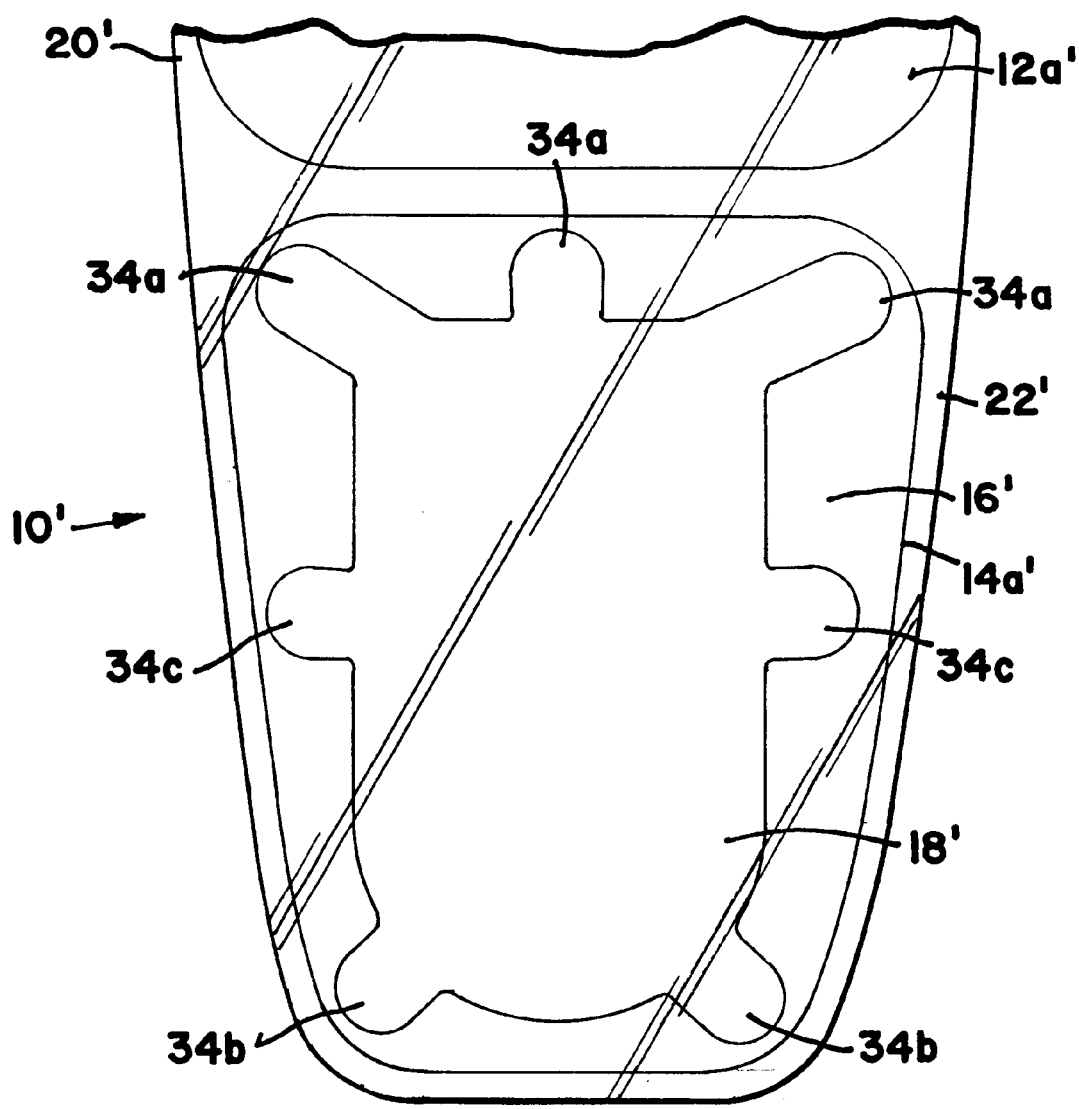

BLADDER FOR ORTHOPEDIC SUPPORTS

FIELD OF THE INVENTION

The present invention relates generally to novel and useful improvements in the field of ankle support braces. In particular, this invention relates to improvements in bladders for orthopedic ankle support braces. The present invention features bladders that are particularly useful as pad members for an ankle support brace. The pad members have an inflated air support pocket and a support pocket formed of a gel material and a filler apparatus. The gel material and filler apparatus are disposed within the interior surface of the support pockets.

BACKGROUND OF THE INVENTION

The use of orthopedic ankle support braces are utilized by a variety of individuals that experience an injury to a limb, such as a leg. Once an injury has been stabilized by, for example, by an immobilizing cast, a removable walking brace can be used to enable exercising of the ankle during healing. A number of such walking braces have been developed for such purpose. The primary goal of such ankle braces is to limit inversion and eversion movement while permitting generally normal dorsi-flexion and plan-to-flexion ankle movements.

An ankle brace configuration that has gained commercial acceptance uses a pair of oppositely disposed generally rigid sidewalls attached near their bottom edges by a flexible base portion that passes below the heel portion of the foot such that the sidewalls cooperatively engage opposite sides of the ankle. The sidewalls are generally contoured to generally match the external shape of the ankle. A pair of support members, typically in the form of pads, air bladders, or gel bladders are placed between the ankle and sidewalls to cushion and support the ankle. The entire brace assembly is secured to the ankle by adjustable fastener straps or lace configurations, and is configured to be worn inside a shoe.

Typical configurations of such a brace are shown in U.S. Pat. No. 4,280,489; 4,628,945 and 5,125,400 to Glen W. Johnson. These braces generally illustrate support-members having various configurations of pneumatic air-inflatable bladders that can be selectively pressurized by the user. One such configuration also includes a porous open-cell pad member within the air bladder to help pre-inflate the bladder while also providing additional cushioning support. Another uses a pair of overlapping inflatable chambers in the bladder in an attempt to better distribute the air within the bladder during use.

U.S. Pat. No. 4,844,094 to Grim illustrates an ankle brace that uses a dense flexible gel cushioning material and which is secured to the shore by the shoe's laces. U.S. Pat. No. 5,007,416 illustrates use of an outer foam pad and an inner gel filled bladder that are secured to one another an to the outer sidewall by a plurality of cooperating fastener patches.

Such known devices have heretofore not provided a simple and cost effective brace configuration that provides adequate support while maintaining wearer comfort. The multiple, overlapping pad, bladder and chamber configurations are relatively expensive to produce, and can be cumbersome to use. Further, a simple cost-effective approach has heretofore not been devised for adequately cushioning the bony portions of the ankle from uncomfortable contact with the hard outer sidewall portions of the brace.

The present invention addresses the above shortcomings of the prior art, and offers a simple, cost effective, and effective brace configuration that is easy to apply and use and yet provides the required comfort and support.

The present invention utilizes a closed cell foam filler disposed with a gel material within a pad support. When a compressive force is applied to the pad support, the gel material moves within the support to accommodate the shape of the user's ankle, but the foam filler remains in place to provide comfort to the ankle's bony portions-providing a stable support for the ankle. The present invention discloses pad support members that have a supporting overlay fastener fabric integrally attached to the pad members across an entire surface thereof, for additional support and for removably and adjustably securing the pad members to the side supports.

These and other features and advantages of the invention will become apparent to those skilled in the art in view of the following description.

SUMMARY OF THE INVENTION

The present invention comprises a therapeutic pad member particularly suitable for use with therapeutic ankle braces. The pad comprising a vinyl pad configuration defining a pre-inflated air support pocket and a second support pocket having a gel material and a filler apparatus disposed within the interior surface of the second support pocket. The filler apparatus material is preferably of closed cell urethane or PVC configuration and cooperates with the gel material to provide uniform support to the lower portion of an ankle. According to one aspect of the invention, the bottom chamber is approximately two-thirds the size of the top chamber. The pad member has a supporting overlay fabric, that acts as a fastener and is integrally attached to the pad member for additional support and for removably securing the pad member to the side supports of an ankle brace.

the bottom chamber is approximately two-thirds the size of the top chamber.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a front view of the improved bladder for orthopedic supports.

FIG. 2 is cross-sectional view in elevation taken along line 2—2 of FIG. 1.

FIG. 4 is a front view of an alternative embodiment of the present invention.

DETAILED DESCRIPTION OF PREFERRED EMBODIMENT

Figure 3:
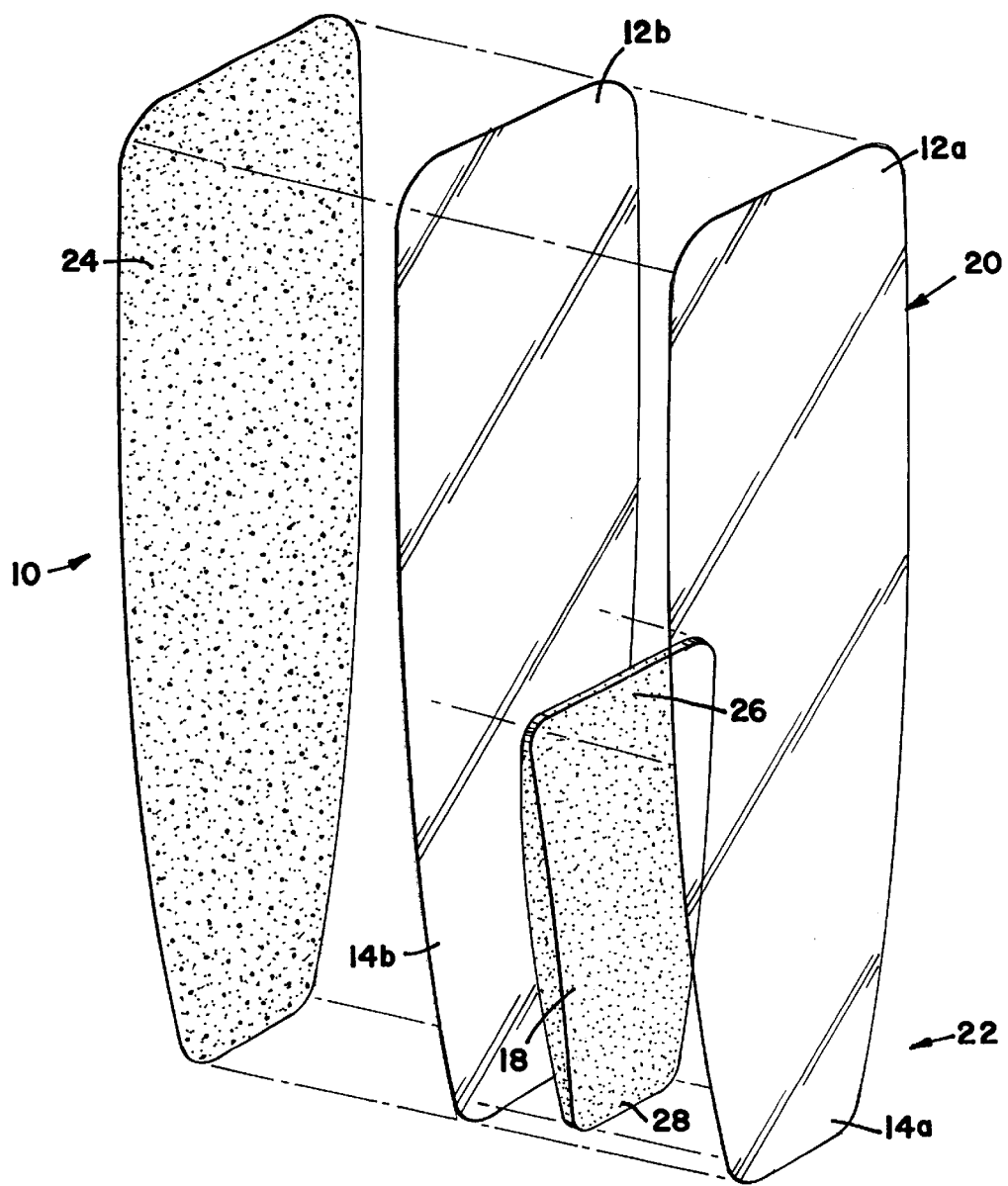
FIG. 3 is an exploded perspective view of the improved bladder for orthopedic supports of the present invention in an assembled relation.

FIG. 1 diagrammatically shows a single flexible, pad member that is utilized in conjunction with a solid side support of a therapeutic ankle support brace. A therapeutic ankle brace adapted for use with this invention is fully described in my copending patent application, Ser. No. 09/243,655, filed Feb. 2, 1999, entitled "Therapeutic Ankle Support Brace" incorporated herein by reference to the extent that the disclosures thereof are necessary to an understanding of this invention.

As shown in FIGS. 1–3, the preferred embodiment disclosed herein illustrates a pad member 10 that has a pair of separate, differently sized, flexible, inflated upper and lower pocket or chamber portions 20 and 22 respectively. A pair of such pads are configured to cooperatively lie adjacent to a pair of generally rigid sidewall members of an ankle brace such as shown in my copending patent application, herein incorporated by reference. Opposed wall member portions 12a, 12b are disposed in juxtaposed, overlapping manner define the top chamber 20 area of the pad member. Opposed wall members 14a, 14b, are disposed in a juxtaposed, overlapping manner define the lower chamber area 22 of the pad member.

Thus, the pad member 10 has associated therewith a top chamber 20 defining an air inflated pocket that is longitudinally connected and contiguous with a lower chamber 22.

In the preferred embodiment, the top chamber 20 is about two-thirds as large as the bottom chamber 22, and the top chamber 20 in conjunction with the bottom chamber 22 are disposed longitudinally to substantially cover a solid sidewall support member, to provide full lateral and medial side support for the ankle.

The pad member 10 of the preferred embodiment of this invention are preferably the type of pad supports used by an ankle brace of the type fully described in my copending patent application as described above. Each pad member comprises a pair of similarly sized, opposed, thin sheets of pliable material (e.g. vinyl, plastic) bonded together along their confronting boundaries in a peripheral configuration generally corresponding to the peripheral shape of a rigid sidewall support with which it will be used. The vinyl sheets are also welded together across a midportion thereof to form the pair of longitudinally spaced and isolated pockets 20, 22. The vinyl sheets may be any suitable vinyl material. In the preferred embodiment vinyl sheets of double polished 10 gauge RF weldable material are used. Materials having hypoallergenic properties may also be used. The bonding may be performed by known joining techniques such as heat or electronic bonding, and is performed more preferably by RF welding techniques.

A filler apparatus or pad 18 of compressible, resilient, non-porous material, preferably closed cell urethane foam or PVC, shaped and sized to substantially extend over the lateral extent of the bottom chamber 22 is disposed interiorly of the outer walls 14a, 14b defining the lower chamber or pocket 22. The filler apparatus or pad 18 is preferably of a non-uniform thickness. The top and bottom edges and 26 and respectively of the filler apparatus are preferably skived or tapered such that they are thinner in comparison to the intermediate portion 30 of the filler apparatus. The thickness differential of the filler apparatus 18 allows for added cushion to the user upon a force being applied to the intermediate portion of the filler apparatus 18 while reducing bulkiness of the lower chamber 22 adjacent its peripheral edges.

During assembly the two thin sheets of pliable material are generally placed in opposing manner with the filler apparatus 18 configured to lie between the inside surfaces of the side portions 14a, 14b, and are bonded by an RF weld along their peripheral confronting boundaries. Upon completion of the RF bond, excess material from the two thin sheets of pliable material are trimmed to size and shape the pad member 10 to its desired shape as illustrated in the Figures. Upon completion of the trimming operation, the top chamber 20 and the bottom chamber 22 are completed by simultaneous forming methods.

First, the top chamber 20, is inflated by piercing the inside panel of pliable material along the central chamber-separating bond line. A predetermined unit of air is inserted into the upper chamber after which the piercing holes are sealed to entrap the inserted air within the upper chamber, thereby pre-inflating the air chamber to a predetermined pressure.

The bottom chamber 22 is completed by piercing the inside panel pliable material along the central chamber separating bond line. A predetermined amount of gel material 16 is inserted into the lower chamber after which the piercing hole is sealed to entrap the gel and filler apparatus materials within the lower chamber 22. The gel material fluidly moves within the bottom chamber and around and over the filler apparatus or pad as compression forces are externally applied to the bottom chamber walls.

Preferably the gel material 16 used may be of an aqueous based solution with properties that are of a viscous and dense nature. In the preferred embodiment, the gel is of a type that is commercially available and used for physical therapy applications. Additionally, the gel material 16 may have thermal properties that allow the gel material 16 to be either preheated or cooled, so as to provide for added therapeutic effect. Alternatively, a non-thermal property gel material 16 may be used to provide for the desired flexibility and comfort for the user due to viscous and dense properties of the gel material 16. Upon a force being applied to a pad member 10 the gel material 16 moves in conjunction with the filler apparatus 18, to provide a firm cushion to the user.

A supporting overlay fabric material having a "loop"-type fastener finish (such as found on Velcro brand fastener materials) 24 is affixed to one entire surface of the pad. In the embodiment illustrated, the fabric fastener material is fastened to the outer surfaces of the 12b and 14b wall portions of the pad. The supporting overlay fastener 24 is affixed through a suitable known application process such as by flame lamination, or by use of a conventional adhesive liquid compound, such that the supporting overlay fastener 24 substantially uniformly adheres to and slightly overlaps the outer periphery of the pad member 10 as depicted in FIGS. 1–3.

The supporting overlay fastener 24 is a fabric material that, in addition to providing a fastener surface, provides additional support to the pad member 10, and may also provide perspiration absorption for the comfort of the user. As shown in my copending application, in order to secure the pad member 10 in a secure position on an ankle brace, the supporting overlay fastener 24 typically fastens to one or more "hook"-type receiving patch(es) secured to the inner surface of a solid sidewall support member of the brace.

An alternative embodiment of a pad configured according to the principles of this invention is disclosed in FIG. 4. wherein parts of the pad illustrated in FIG. 4 are designated by the same numerals used in FIGS. 1–3, followed by a prime (') designation. In the alternative embodiment, a pad member 10' is formed generally according to the same steps and in the same general configuration as previously described with respect to the first-described embodiment, with the exception of the shape of the filler apparatus 18'. The filler apparatus or pad 18' includes a plurality of extensions or prongs 34. In other respects, the filler apparatus is of similar material and construction to that of the filler apparatus 18 previously described with respect to the first embodiment.

The top and bottom extending prongs 34a and 34b respectively engage the lower chamber walls at the top and bottom ends of the chamber to hinder longitudinal movement of the filler apparatus within the chamber. The side extending prongs 34c engage the sides of the chamber to hinder transverse movement of the filler apparatus within the chamber.

The foregoing description of the invention has been presented for purposes of illustration and description, and is not intended to be exhaustive or to limit the invention to the precise form disclosed. The description was selected to explain the principles of the invention in various embodiments and various modifications as are suited to the particular use contemplated. It is intended that the scope of the invention not be limited by the specification, but defined by the claims set forth below:

The claimed invention is:

1. An improved bladder for orthopedic supports comprising:
   a pair of opposed flexible sidewalls of pliable sheet material bonded together to form a first, inflated air support pocket and a second sealed support pocket containing a fluid gel material and a solid foam pad intermixed together within a sealed interior chamber of the second support pocket.

2. The apparatus of claim 1, wherein the first and second support pockets comprise a top chamber and a bottom chamber of said bladder.

3. The apparatus of claim 2, wherein the top chamber comprises said first pocket and wherein said bottom chamber comprises said second pocket.

4. The apparatus of claim 3, wherein said top chamber comprises a sealed pre-inflated air pocket.

5. The apparatus of claim 3, wherein said bottom chamber is approximately two-thirds the size of said top chamber.

6. The apparatus of claim 3, wherein the foam pad comprises closed cell urethane foam.

7. The apparatus of claim 6, wherein the foam pad is of non-uniform thickness.

8. The apparatus of claim 7 wherein at least one peripheral edge of said foam pad material has a thickness substantially less than that of an intermediate portion of said foam pad apparatus.

9. The apparatus of claim 3, wherein said fluid gel material has thermal properties capable of retaining heat or cold.

10. The apparatus of claim 3, wherein said opposed sidewalls defining said first and second pockets comprise vinyl sheet materials superimposed and bonded together along their peripheral extents.

11. The apparatus of claim 10, wherein the said first chamber is inflated with a predetermined unit of air and sealed.

12. The apparatus of claim 10, wherein the gel material within said second chamber is in fluid communication with the foam pad.

13. The apparatus of claim 1, wherein the bladder may be folded about itself to form a transverse fold extending substantially perpendicular to the longitudinal boundaries of the pair of sidewalls intermedially of the longitudinal extent of the sidewalls.

14. An improved bladder for orthopedic supports comprising:
   a pair of opposed flexible sidewalls defining a sealed support pocket containing a gel material and a filler apparatus, said filler apparatus having a main body portion and prongs extending outwardly therefrom, said prongs being configured to engage an interior surface of the support pocket for maintaining the main body portion of said filler apparatus at a predetermined position within said support pocket; and
   a supporting overlay fastener integrally attached to one of the sidewalls, to provide additional support and to removably secure the bladder to an external support surface.

15. The apparatus of claim 14, wherein the filler apparatus with extending prongs is a closed cell urethane foam.

16. The apparatus of claim 14, wherein the filler apparatus is of non-uniform thickness.

17. The apparatus of claim 1, further including a supporting overlay fabric fastener integrally attached to one of said sidewalls and extending substantially across the entire surface of said one sidewall, said fabric fastener providing additional support to the bladder and a fastening surface for removably securing the bladder to an external support surface.

* * * * *

UNITED STATES PATENT AND TRADEMARK OFFICE
CERTIFICATE OF CORRECTION

PATENT NO. : 6,306,112 B2
DATED : October 23, 2001
INVENTOR(S) : Bird

It is certified that error appears in the above-identified patent and that said Letters Patent is hereby corrected as shown below:

Title page,
Item [57], ABSTRACT,
Line 2, insert -- of -- between "pair" and "opposed".

Column 1,
Line 20, after "example", delete "by".
Line 53, change "shore" to -- shoe --.

Column 2,
Line 8, replace the hyphen "-" with a comma -- , --.
Line 23, replace "comprising" with -- comprises --.
Lines 36 and 37, delete redundant sentence fragment beginning with "the" and ending with "chamber".

Column 3,
Lines 9 and 11, delete the words "are".
Line 48, delete "and".
Line 49, after "and" insert -- 28 --.

Column 4,
Line 50, change "patch(s)" to -- patch(es) --.

Signed and Sealed this

Twenty-seventh Day of May, 2003

JAMES E. ROGAN
*Director of the United States Patent and Trademark Office*